United States Patent
Schnatterer et al.

(10) Patent No.: US 8,710,238 B2
(45) Date of Patent: Apr. 29, 2014

(54) CIS-ALKOXY-SUBSTITUTED SPIROCYCLIC 1-H-PYRROLIDINE-2,4-DIONE DERIVATIVES

(75) Inventors: Albert Schnatterer, Leverkusen (DE); Thomas Himmler, Odenthal (DE); Reiner Fischer, Monheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/004,404

(22) PCT Filed: Mar. 6, 2012

(86) PCT No.: PCT/EP2012/053810
§ 371 (c)(1),
(2), (4) Date: Nov. 18, 2013

(87) PCT Pub. No.: WO2012/123287
PCT Pub. Date: Sep. 20, 2012

(65) Prior Publication Data
US 2014/0058114 A1  Feb. 27, 2014

Related U.S. Application Data

(60) Provisional application No. 61/451,783, filed on Mar. 11, 2011.

(30) Foreign Application Priority Data

Mar. 11, 2011  (EP) .................................. 11157904

(51) Int. Cl.
*C07D 235/02* (2006.01)
(52) U.S. Cl.
CPC .................... *C07D 235/02* (2013.01)
USPC .................................................... 548/301.4
(58) Field of Classification Search
CPC ........................................................ C07D 235/02
USPC ............................................................ 548/301.4
See application file for complete search history.

(56) References Cited

U.S. PATENT DOCUMENTS

| | | | |
|---|---|---|---|
| 5,462,913 A | 10/1995 | Fischer et al. | |
| 5,622,917 A | 4/1997 | Fischer et al. | |
| 5,677,449 A | 10/1997 | Fischer et al. | |
| 5,830,826 A | 11/1998 | Fischer et al. | |
| 5,847,211 A | 12/1998 | Fischer et al. | |
| 5,994,274 A | 11/1999 | Fischer et al. | |
| 6,110,872 A | 8/2000 | Lieb et al. | |
| 6,114,374 A | 9/2000 | Lieb et al. | |
| 6,140,358 A | 10/2000 | Lieb et al. | |
| 6,172,255 B1 | 1/2001 | Fischer et al. | |
| 6,251,830 B1 | 6/2001 | Fischer et al. | |
| 6,255,342 B1 | 7/2001 | Lieb et al. | |
| 6,271,180 B2 | 8/2001 | Lieb et al. | |
| 6,316,486 B1 | 11/2001 | Lieb et al. | |
| 6,358,887 B1 | 3/2002 | Fischer et al. | |
| 6,359,151 B2 | 3/2002 | Lieb et al. | |
| 6,380,246 B1 | 4/2002 | Lieb et al. | |
| 6,388,123 B1 | 5/2002 | Lieb et al. | |
| 6,417,370 B1 | 7/2002 | Lieb et al. | |
| 6,451,843 B1 | 9/2002 | Lieb et al. | |
| 6,469,196 B2 | 10/2002 | Fischer et al. | |
| 6,472,419 B1 | 10/2002 | Fischer et al. | |
| 6,486,343 B1 | 11/2002 | Lieb et al. | |
| 6,504,036 B1 | 1/2003 | Lieb et al. | |
| 6,511,942 B1 | 1/2003 | Lieb et al. | |
| 6,596,873 B1 | 7/2003 | Lieb et al. | |
| 6,693,092 B2 | 2/2004 | Lieb et al. | |
| 6,716,832 B2 | 4/2004 | Lieb et al. | |
| 6,746,990 B2 | 6/2004 | Fischer et al. | |
| 6,759,548 B2 | 7/2004 | Fischer et al. | |
| 6,767,864 B2 | 7/2004 | Fischer et al. | |
| 6,806,264 B2 | 10/2004 | Lieb et al. | |
| 6,858,741 B2 | 2/2005 | Lieb et al. | |
| 6,933,261 B2 | 8/2005 | Lieb et al. | |
| 6,939,888 B2 | 9/2005 | Fischer et al. | |
| 7,105,471 B2 | 9/2006 | Lieb et al. | |
| 7,141,533 B2 | 11/2006 | Fischer et al. | |
| 7,148,377 B2 | 12/2006 | Himmler et al. | |
| 7,230,116 B2 | 6/2007 | Fischer et al. | |
| 7,256,158 B2 | 8/2007 | Lieb et al. | |
| 7,288,676 B2 | 10/2007 | Lieb et al. | |
| 7,435,829 B2 | 10/2008 | Fischer et al. | |
| 7,511,153 B2 | 3/2009 | Himmler et al. | |
| 7,638,547 B2 | 12/2009 | Himmler et al. | |
| 7,642,359 B2 | 1/2010 | Fischer et al. | |
| 7,718,186 B2 | 5/2010 | Fischer et al. | |
| 7,718,706 B2 | 5/2010 | Lieb et al. | |
| 7,727,933 B2 | 6/2010 | Fischer et al. | |
| 7,776,791 B2 | 8/2010 | Fischer et al. | |
| 7,803,967 B2 | 9/2010 | Himmler et al. | |
| 7,897,803 B2 | 3/2011 | Himmler et al. | |
| 7,915,282 B2 | 3/2011 | Ruther et al. | |
| 7,947,704 B2 | 5/2011 | Bretschneider et al. | |
| 8,013,172 B2 | 9/2011 | Fischer et al. | |
| 8,058,210 B2 | 11/2011 | Lieb et al. | |
| 8,058,452 B2 | 11/2011 | Fischer et al. | |
| 8,193,120 B2 | 6/2012 | Ruther et al. | |
| 8,334,300 B2 | 12/2012 | Ruther et al. | |
| 8,383,853 B2 | 2/2013 | Fischer et al. | |
| 8,518,985 B2 | 8/2013 | Fischer et al. | |

(Continued)

FOREIGN PATENT DOCUMENTS

EP  0596298  11/1994
EP  0668267  8/1995

(Continued)

OTHER PUBLICATIONS

International Search Report for PCT/EP2012/053810 Mailed April 16, 2012.

*Primary Examiner* — Laura L. Stockton (74) *Attorney, Agent, or Firm* — Miles & Stockbridge PC (57) ABSTRACT

Process for preparing cis-alkoxy-substituted spirocyclic 1-H-pyrrolidine-2,4-dione derivatives and alkali metal salts and alkaline earth metal salts thereof.

9 Claims, 5 Drawing Sheets

(56) References Cited

U.S. PATENT DOCUMENTS

| | | |
|---|---|---|
| 2001/0004629 A1 | 6/2001 | Lieb et al. |
| 2002/0010204 A1 | 1/2002 | Lieb et al. |
| 2002/0022575 A1 | 2/2002 | Fischer et al. |
| 2002/0188136 A1 | 12/2002 | Lieb et al. |
| 2003/0045432 A1 | 3/2003 | Fischer et al. |
| 2003/0073851 A1 | 4/2003 | Lieb et al. |
| 2003/0096806 A1 | 5/2003 | Lieb et al. |
| 2003/0144504 A1 | 7/2003 | Fischer et al. |
| 2003/0171219 A1 | 9/2003 | Lied et al. |
| 2003/0199572 A1 | 10/2003 | Lieb et al. |
| 2003/0216260 A1 | 11/2003 | Ruther et al. |
| 2004/0009877 A1 | 1/2004 | Fischer et al. |
| 2004/0019061 A1 | 1/2004 | Fischer et al. |
| 2004/0039223 A1 | 2/2004 | Himmler et al. |
| 2004/0127365 A1 | 7/2004 | Lieb et al. |
| 2004/0167031 A1 | 8/2004 | Lieb et al. |
| 2004/0220243 A1 | 11/2004 | Fischer et al. |
| 2004/0242664 A1 | 12/2004 | Fischer et al. |
| 2005/0038021 A1 | 2/2005 | Lieb et al. |
| 2005/0164885 A1 | 7/2005 | Lieb et al. |
| 2006/0122061 A1 | 6/2006 | Lieb et al. |
| 2006/0160847 A1 | 7/2006 | Fischer et al. |
| 2006/0166829 A1 | 7/2006 | Fischer et al. |
| 2007/0032539 A1 | 2/2007 | Himmler |
| 2007/0043219 A1 | 2/2007 | Himmler et al. |
| 2007/0129252 A1 | 6/2007 | Fischer et al. |
| 2007/0203101 A1 | 8/2007 | Fischer et al. |
| 2007/0244007 A1 | 10/2007 | Fischer et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |
| 2008/0220973 A1 | 9/2008 | Fischer et al. |
| 2008/0293573 A1 | 11/2008 | Fischer et al. |
| 2008/0318776 A1 | 12/2008 | Fischer et al. |
| 2009/0156402 A1 | 6/2009 | Himmler et al. |
| 2009/0305891 A1 | 12/2009 | Fischer et al. |
| 2010/0009850 A1 | 1/2010 | Fischer et al. |
| 2010/0056598 A1 | 3/2010 | Himmler et al. |
| 2010/0062942 A1 | 3/2010 | Fischer et al. |
| 2010/0087320 A1 | 4/2010 | Lieb et al. |
| 2010/0174084 A1 | 7/2010 | Fischer et al. |
| 2010/0261934 A1 | 10/2010 | Fischer et al. |
| 2010/0267964 A1 | 10/2010 | Fischer et al. |
| 2010/0311593 A1 | 12/2010 | Fischer et al. |
| 2011/0130284 A1 | 6/2011 | Fischer et al. |
| 2011/0143942 A1 | 6/2011 | Fischer et al. |
| 2011/0143943 A1 | 6/2011 | Ruther et al. |
| 2011/0183849 A1 | 7/2011 | Ruther et al. |
| 2011/0195842 A1 | 8/2011 | Bretschneider et al. |
| 2011/0213160 A1 | 9/2011 | Bretschneider et al. |
| 2012/0178927 A1 | 7/2012 | Fischer et al. |
| 2012/0238450 A1 | 9/2012 | Ruther et al. |

FOREIGN PATENT DOCUMENTS

| | | |
|---|---|---|
| WO | 9520572 | 8/1995 |
| WO | 9526954 | 10/1995 |
| WO | 9625395 | 8/1996 |
| WO | 9635664 | 11/1996 |
| WO | 9701535 | 1/1997 |
| WO | 9702243 | 1/1997 |
| WO | 9736868 | 10/1997 |
| WO | 9805638 | 2/1998 |
| WO | 9943649 | 9/1999 |
| WO | 9948869 | 9/1999 |
| WO | 9955673 | 11/1999 |
| WO | 0174770 | 11/2001 |
| WO | 0196333 | 12/2001 |
| WO | 0202532 | 1/2002 |
| WO | 03035643 | 10/2002 |
| WO | 2004007448 | 1/2004 |
| WO | 2004065366 | 8/2004 |
| WO | 2004111042 | 12/2004 |
| WO | 2005044796 | 5/2005 |
| WO | 2005049569 | 6/2005 |
| WO | 2005066125 | 7/2005 |
| WO | 2005092897 | 10/2005 |
| WO | 2006029799 | 3/2006 |
| WO | 2006056281 | 6/2006 |
| WO | 2006056282 | 6/2006 |
| WO | 2007096058 | 8/2007 |
| WO | 2008067910 | 6/2008 |
| WO | 2008138551 | 11/2008 |
| WO | 2010102758 | 9/2010 |

CIS-ALKOXY-SUBSTITUTED SPIROCYCLIC 1-H-PYRROLIDINE-2,4-DIONE DERIVATIVES

CROSS REFERENCE TO RELATED APPLICATIONS

This application is a §371 National Stage Application of PCT/EP2012/053810, filed Mar. 6, 2012, which claims priority to European Application No. 11157904.1, filed Mar. 11, 2011, and U.S. Provisional Application No. 61/451,783, filed Mar. 11, 2011.

BACKGROUND OF THE INVENTION

1. Field of the Invention

The present invention relates to processes for preparing cis-alkoxy-substituted spirocyclic 1-H-pyrrolidine-2,4-dione derivatives and alkali metal salts and alkaline earth metal salts thereof.

2. Description of Related Art

Alkoxy-substituted spirocyclic 1-H-pyrrolidine-2,4-dione derivatives of the general formula (I) having acaricidal, insecticidal and herbicidal action are known: EP-A 596 298, WO95/20572, WO 95/26954, WO 95/20572, EP-A 668 267, WO 96/25395, WO 96/35664, WO 97/01535, WO 97/02243, WO 97/36868, WO 98/05638, WO 99/43649, WO 99/48869, WO 99/55673, WO 01/74770, WO 01/96333, WO 03/035643, WO 04/007448, WO 04/065366, WO 04/111042, WO 05/066125, WO 05/049569, WO 05/044796, WO 05/092897, WO 06/056282, WO 06/056281, WO 06/029799, WO 07/096,058, WO 08/067,910, WO 08/138,551, WO 10/102,758.

Such compounds are usually prepared starting with the corresponding cis-substituted hydantoins of the formula (cis-II).

In the formulae (I), (II) and (cis-II),

V, W, X, Y and Z independently of one another represent hydrogen, alkyl, halogen, alkoxy, haloalkyl or haloalkoxy, A represents $C_1$-$C_6$-alkyl, G represents hydrogen (a) or represents one of the groups in which

L represents oxygen or sulphur, $R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl or represents thienyl,

$R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl.

It is already known that in particular the cis-substituted compounds of the formula (I) have biologically advantageous properties (activity, toxicological profile) (WO2004/007448). Accordingly, there is an increased demand for cis-substituted hydantoins of the formula (cis-II) as starting materials.

However, owing to the preparation processes, the known compounds of the formula (II) are generally obtained in the form of cis/trans isomer mixtures.

It is also already known (WO2002/02532) that, from an isomer mixture of the formula (II), the desired cis isomer (cis-II) can be obtained in high purity by stirring the isomer mixture with aqueous ammonia, which apparently results in the formation of the ammonium salts of the formula (III). Since the solubility of the cis salts (cis-III) is considerably lower than that of the trans salts (trans-III), the salts (cis-III) or the hydantoins (cis-II) can be isolated in high purity by filtration.

However, this process has a number of disadvantages: the amount of ammonia required is high (multiple molar excess); the use of ammonia results in a drastically increased nitrogen load of the wastewater, which is unwanted and may require expensive work-up of the wastewater; the base strength of ammonia is insufficient for the subsequent hydrolysis of the hydantoin under temperature and pressure conditions acceptable for production on an industrial scale, so that direct further processing of (cis-III) is not possible.

Accordingly, there was still a need for a process for separating isomers of compounds of the formula (II), which process is simpler, better to realize on an industrial scale and more environmentally friendly.

SUMMARY

We have now found a novel process for isolating cis-hydantoins of the formula (cis-II), which process is characterized in that an isomer mixture of the formula (II) is stirred with an aqueous solution of an alkali metal hydroxide or alkaline earth metal hydroxide and the cis isomer is then isolated.

This gives, depending on the chosen alkali metal hydroxide or alkaline earth metal hydroxide and the isolation conditions (temperature, washing of the solid with water), compounds (cis-II), the corresponding salts (cis-IV) or mixtures of (cis-II) and (cis-IV).

The present invention also provides novel alkali metal salts and alkaline earth metal salts of the formulae (cis-IV) and (trans-IV) which have highly different solubilities in water and, by virtue of these properties, allow (cis-IV) and/or (cis-II) to be isolated. The compounds of the formulae (cis-IV) and (trans-IV) can also be present as corresponding hydrates, which also form part of the subject matter of the invention.

Here, in the formulae (IV),
A represents $C_1$-$C_6$-alkyl,
M represents an alkali metal cation or an alkaline earth metal cation
and
n represents 1 if M is an alkali metal cation
or
represents 2 if M is an alkaline earth metal cation.
The other possible mesomeric structures of the compounds of the formula (IV) are meant to be embraced by this formula.
Preferably,
A represents $C_1$-$C_4$-alkyl,
M represents an alkali metal cation and
n represents 1.
Particularly preferably,
A represents methyl, ethyl, propyl, isopropyl, butyl or isobutyl (very particularly preferably methyl),
M represents $Li^+$, $Na^+$ or $K^+$
and
n represents 1.
In the definitions of the symbols given in the formulae above, collective terms were used which are generally representative for the following substituents:
Alkyl: saturated, straight-chain or branched hydrocarbon radicals having 1 to 6 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

DETAILED DESCRIPTION OF A PREFERRED EMBODIMENT

The general or preferred radical definitions or illustrations given above can be combined with one another as desired, i.e. including combinations between the respective ranges and preferred ranges. They apply both to the end products and, correspondingly, to the precursors and intermediates.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals may be mono- or polysubstituted, where in the case of polysubstitution the substituents may be identical or different.

In addition to the compounds mentioned in the Preparation Examples, the following compounds of the formula (cis-IV) may be specifically mentioned:

(cis-IV)

TABLE 1

| A | M | n |
|---|---|---|
| $C_2H_5$ | $Li^+$ | 1 |
| $C_2H_5$ | $Na^+$ | 1 |
| $C_2H_5$ | $K^+$ | 1 |
| $C_2H_5$ | $Rb^+$ | 1 |
| $C_2H_5$ | $Be^{2+}$ | 2 |
| $C_2H_5$ | $Mg^{2+}$ | 2 |
| $C_2H_5$ | $Ca^{2+}$ | 2 |
| $C_2H_5$ | $Sr^{2+}$ | 2 |
| $C_2H_5$ | $Ba^{2+}$ | 2 |
| $C_3H_7$ | $Na^+$ | 1 |
| $C_3H_7$ | $K^+$ | 1 |
| $iC_3H_7$ | $Na^+$ | 1 |
| $iC_3H_7$ | $K^+$ | 1 |
| $C_4H_9$ | $Na^+$ | 1 |
| $C_4H_9$ | $K^+$ | 1 |
| $iC_4H_9$ | $Na^+$ | 1 |
| $iC_4H_9$ | $K^+$ | 1 |

The compounds of the formula (II) required as starting materials for the process according to the invention are known and can be prepared by known methods (Strecker synthesis; Bucherer-Bergs reaction).

The compounds of the formula (cis-IV) or (cis-II) are obtained by reacting hydantoins of the formula (II)

(II)

in which
A has the meanings given above,
in a diluent with an alkali metal hydroxide or alkaline earth metal hydroxide and then removing the compound of the formula (cis-IV) or (cis-II).

The diluent used in the process according to the invention is water.

Suitable alkali metal hydroxides or alkaline earth metal hydroxides for carrying out the process according to the invention are all known alkali metal hydroxides or alkaline earth metal hydroxides. Preference is given to using lithium hydroxide, sodium hydroxide, potassium hydroxide, cesium hydroxide, magnesium hydroxide, rubidium hydroxide, calcium hydroxide or barium hydroxide. Particular preference is given to sodium hydroxide, lithium hydroxide and potassium hydroxide. Very particular preference is given to sodium hydroxide and potassium hydroxide.

When carrying out the process according to the invention, the hydantoin of the formula (II) and the alkali metal hydroxide or alkaline earth metal hydroxide are generally employed in molar ratios such that the molar amount of alkali metal hydroxide corresponds to the molar proportion of (cis-II) in the isomer mixture (II), or that the molar amount of alkaline earth metal hydroxide is half the molar proportion of (cis-II) in the isomer mixture (II). However, it is also possible to use a relatively large excess (up to 2 mol) of one component or the other.

When carrying out the process according to the invention, the reaction temperature can be varied within a relatively wide range. In general, the process is carried out at temperatures between 0° C. and 100° C., preferably between 10° C. and 90° C.

The process according to the invention is generally carried out under atmospheric pressure.

The practice of the process according to the invention and the preparation of the compounds according to the invention are shown in the examples below, without being limited thereby.

PREPARATION EXAMPLES

Example 1

Using LiOH

A suspension consisting of 19.84 g (0.1 mol) of the compound (II, A=Me; purity 99.9%; isomer ratio cis/trans=75:25) and 1.857 g (0.076 mol) of LiOH (98% pure) in 48 ml of water is stirred at 80° C. for 30 minutes. The mixture is then allowed to cool to room temperature, and the solid is filtered off with suction, washed with 10 ml of water and dried. This gives 9.23 g of the compound (II) having an isomer ratio cis/trans of 99.9:0.1.

Figure 1:
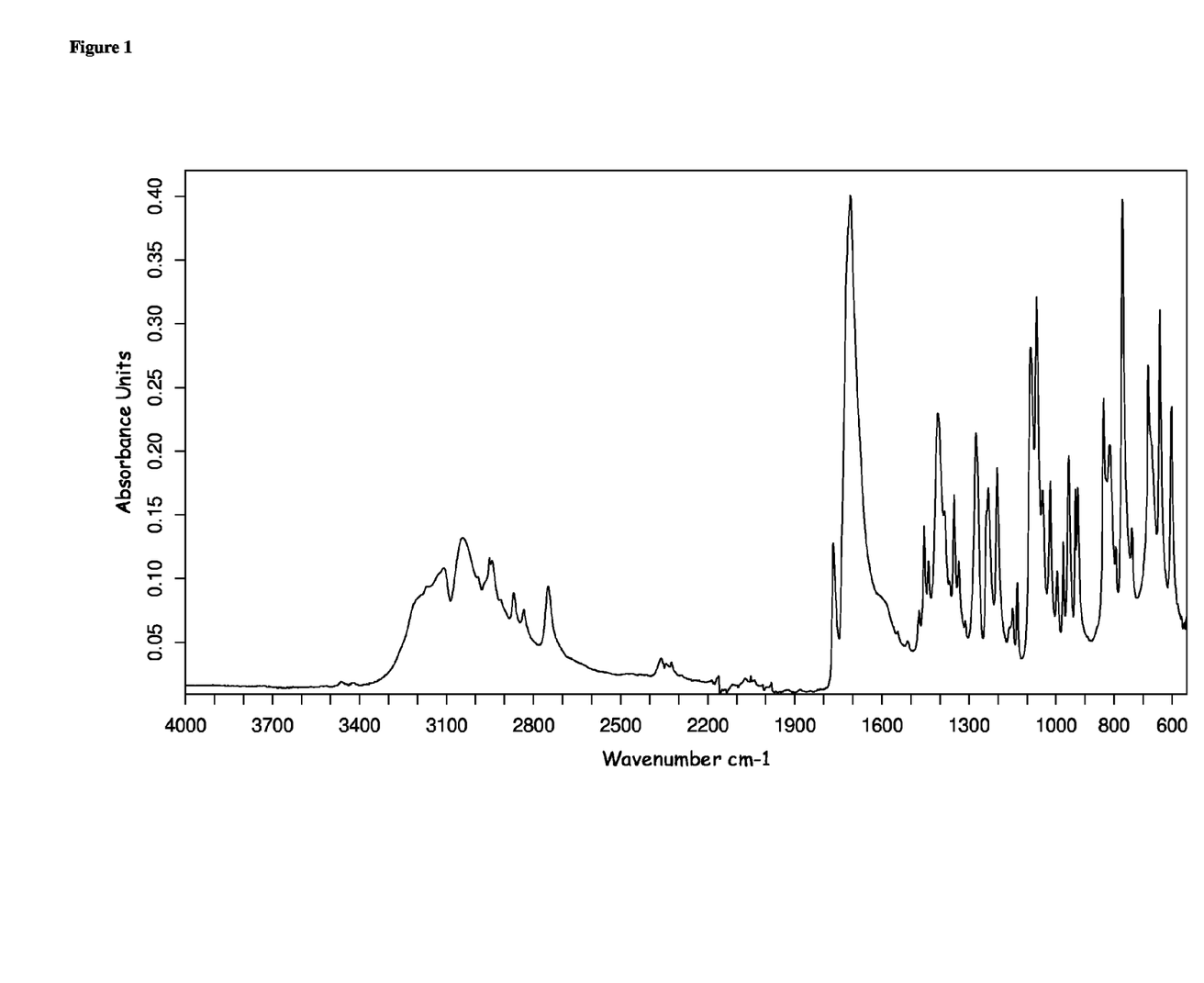
FIGS. 1-5 represent embodiments as described herein.

The IR spectrum of the compound (cis-II) is shown in FIG. 1.
Intensive bands: 1767 cm$^{-1}$, 1709 cm$^{-1}$, 1407 cm$^{-1}$, 1276 cm$^{-1}$, 1233 cm$^{-1}$, 1203 cm$^{-1}$, 1087 cm$^{-1}$, 1067 cm$^{-1}$, 836 cm$^{-1}$, 815 cm$^{-1}$, 771 cm$^{-1}$, 682 cm$^{-1}$, 642 cm$^{-1}$, 602 cm$^{-1}$.

Example 2

Using NaOH

Figure 2:
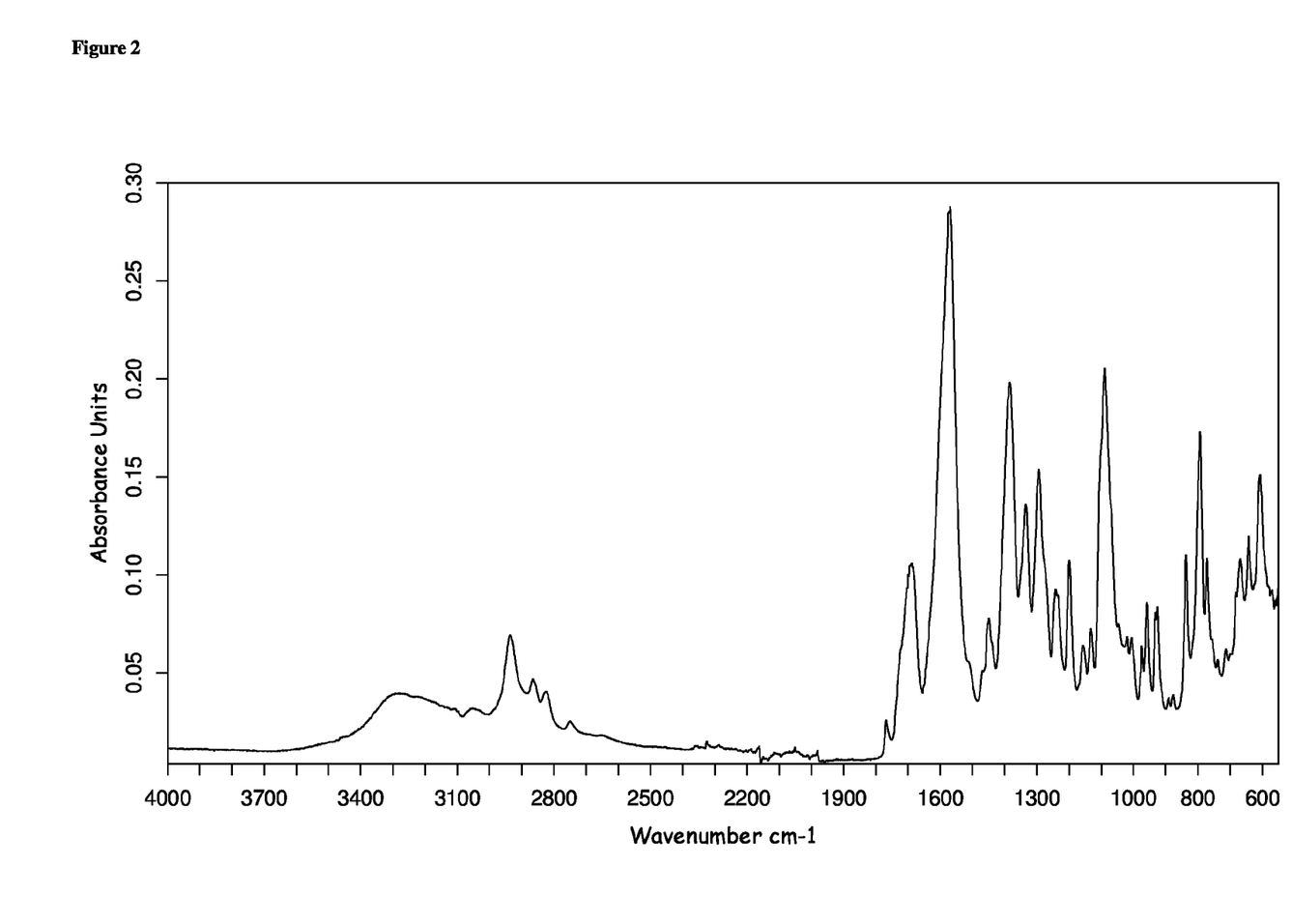

A suspension consisting of 19.84 g (0.1 mol) of the compound (II, A=Me; purity 99.9%; isomer ratio cis/trans=75:25) and 3.04 g (0.076 mol) of NaOH in 48 ml of water is stirred at 80° C. for 30 minutes. The mixture is then allowed to cool to room temperature and stirred for a further 30 minutes, and the solid is filtered off with suction, washed with 10 ml of water and dried. This gives 12.26 g of a solid having an isomer ratio cis/trans of 95.0:5.0 and a water content of 0.6% by weight.
Ion chromatography showed a sodium content of 7.07% by weight (theoretical: 10.4%); i.e. the product is predominantly a mixture of (cis-II) and (cis-IV).
The IR spectrum of the product is shown in FIG. 2.
The following bands are characteristic for the sodium salt (cis-IV, M=Na, n=1):
1687 cm$^{-1}$, 1573 cm$^{-1}$, 1386 cm$^{-1}$, 1334 cm$^{-1}$, 1295 cm$^{-1}$, 1090 cm$^{-1}$, 793 cm$^{-1}$.

Example 3

Using NaOH 100 g of a crude cis/trans mixture of the compound II (where A=Me) comprising, as main components, 66.9% by weight of cis isomer and 22.6% by weight of trans isomer are, together with 342 g of a 4% strength aqueous sodium hydroxide solution, heated to 80° C. From about 70° C. onwards, a clear solution is formed. On subsequent cooling of the solution, spontaneous crystallization sets in at about 45° C. Cooling of the crystal suspension is continued to about 20° C. The crystalline solid is filtered off with suction, washed twice with in each case 50 ml of water and dried. This gives 43.5 g of solid having a content of compounds II and IV (M=Na) which, in total, corresponds to 91.0% by weight of II, at an isomer ratio cis/trans of 97.5:2.5.

Example 4

Using NaOH 100 g of a crude cis/trans mixture of the compound II (where A=Me) comprising, as main components, 66.9% by weight of cis isomer and 22.6% by weight of trans isomer are, together with 452 g of a 6% strength aqueous sodium hydroxide solution, heated to 80° C. From about 60° C. onwards, a clear solution is formed. On subsequent cooling of the solution, spontaneous crystallization sets in at about 50° C. Cooling of the crystal suspension is continued to about 20° C. The crystalline solid is filtered off with suction, washed twice with in each case 75 ml of water and dried. This gives 80.4 g of solid having a content of compounds II and IV (M=Na) which, in total, corresponds to 87.3% by weight of II, at an isomer ratio cis/trans of 97.5:2.5.

Example 5

Using NaOH 100 g of a crude cis/trans mixture of the compound II (where A=Me) comprising, as main components, 66.9% by weight of cis isomer and 22.6% by weight of trans isomer are, together with 484 g of a 7% strength aqueous sodium hydroxide solution, heated to 80° C. From about 70° C. onwards, a clear solution is formed. On subsequent cooling of the solution, spontaneous crystallization sets in at about 50° C. Cooling of the crystal suspension is continued to about 20° C. The crystalline solid is filtered off with suction, washed with 150 ml of water and dried. This gives 76.4 g of solid having a content of compounds II and IV (M=Na) which, in total, corresponds to 90.6% by weight of II, at an isomer ratio cis/trans of 96.9:3.1.

Example 6

Using KOH

Figure 3:
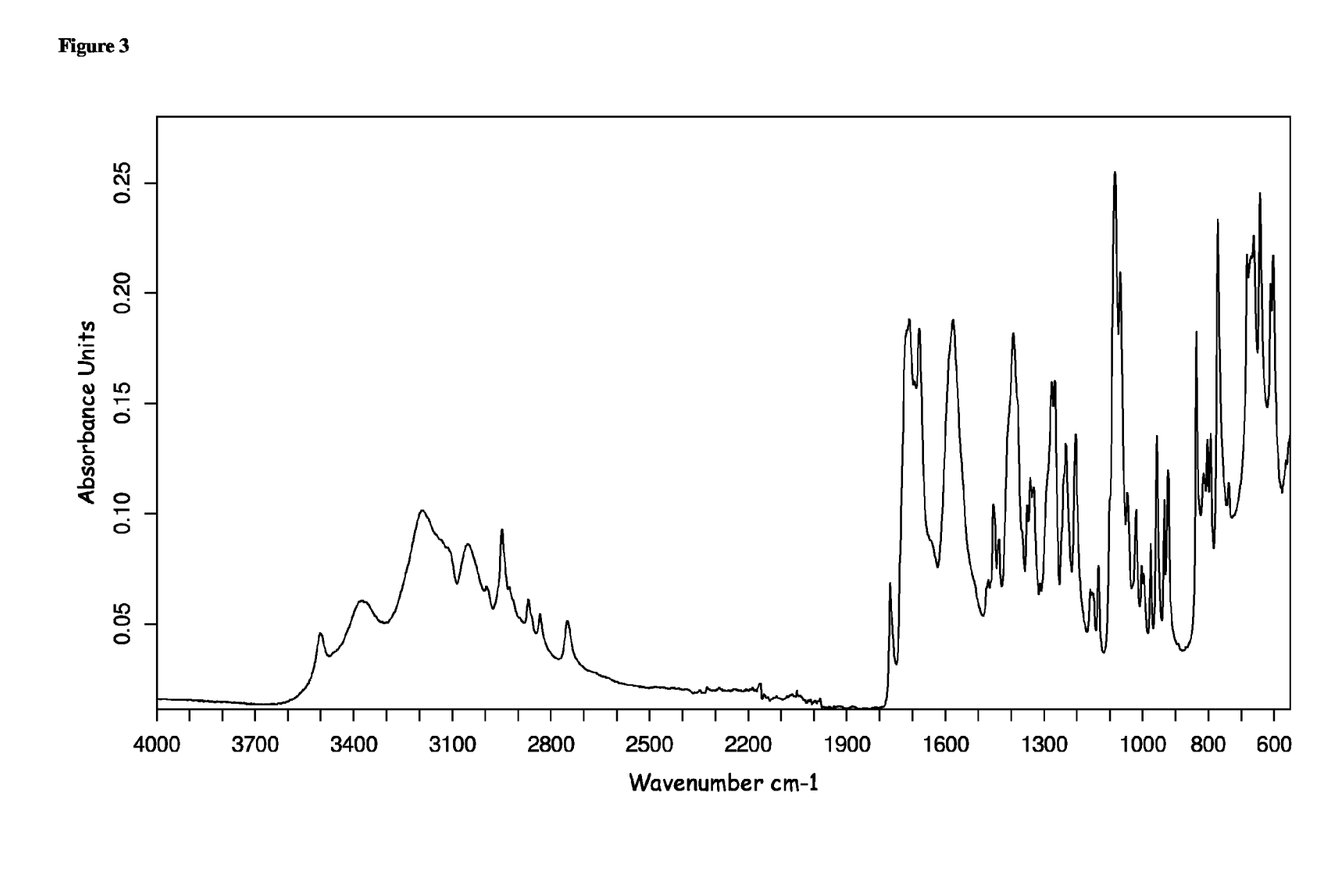

A suspension consisting of 19.84 g (0.1 mol) of the compound (II, A=Me; purity 99.9%; isomer ratio cis/trans=75:25) and 5.016 g (0.076 mol) of KOH (85% pure) in 48 ml of water is stirred at 80° C. for 30 minutes. The mixture is then allowed to cool to room temperature and stirred for a further 30 minutes, and the solid is filtered off with suction, washed with 10 ml of water and dried. This gives 7.86 g of solid having an isomer ratio cis/trans of 98.3:1.7 and a water content of 10.28% by weight.
Ion chromatography showed a potassium content of 8.7% by weight (theoretical: 16.55%); i.e. the product is predominantly a mixture of (cis-II) and (cis-IV).
The IR spectrum of the product is shown in FIG. 3.
The following bands are characteristic for the potassium salt (cis-IV, M=K, n=1): 1679 cm$^{-1}$, 1576 cm$^{-1}$, 1393 cm$^{-1}$, 1267 cm$^{-1}$.

Example 7

Using RbOH

A suspension consisting of 19.84 g (0.1 mol) of the compound (II, A=Me; purity 99.9%; isomer ratio cis/trans=75:25) and 15.73 g (0.076 mol) of RbOH (50% strength aqueous solution) in 40 ml of water is stirred at 80° C. for 30 minutes. The mixture is then allowed to cool to room temperature and stirred for a further 30 minutes, and the solid is filtered off with suction, washed with 10 ml of water and dried. This gives 3.63 g of solid having an isomer ratio cis/trans of 99.3:0.7 and a water content of 0.44% by weight.
Elemental analysis showed a rubidium content of 0.17% by weight (theoretical: 30.23%); i.e. the product is virtually exclusively (cis-II).

Example 8

Using CsOH

A suspension consisting of 19.84 g (0.1 mol) of the compound (II, A=Me; purity 99.9%; isomer ratio cis/trans=75:25) and 23.02 g (0.076 mol) of CsOH (50% strength aqueous solution) in 36 ml of water is stirred at 80° C. for 30 minutes. The mixture is then allowed to cool to room temperature and stirred for a further 30 minutes, and the solid is filtered off with suction, washed with 10 ml of water and dried. This gives 3.78 g of solid having an isomer ratio cis/trans of 99.2:0.8 and a water content of 0.11% by weight.
Elemental analysis showed a cesium content of 0.18% by weight (theoretical: 40.26%); i.e. the product is virtually exclusively (cis-II).

Example 9

Using Ca(OH)$_2$

A suspension consisting of 19.84 g (0.1 mol) of the compound (II, A=Me; purity 99.9%; isomer ratio cis/trans=75:25) and 2.873 g (0.038 mol) of Ca(OH)$_2$ (98% pure) in 48 ml of water is stirred at 80° C. for 30 minutes. A further 15 ml of water are then added, the mixture is allowed to cool to room temperature and stirred for a further 30 minutes and the solid is filtered off with suction, washed with 10 ml of water and dried. This gives 16.98 g of solid having an isomer ratio cis/trans of 88:12 and a water content of 3.08% by weight.

Elemental analysis showed a calcium content of 5.7% by weight (theoretical: 9.2%); i.e. the product is predominantly a mixture of (cis-II) and (cis-IV).

Figure 4:
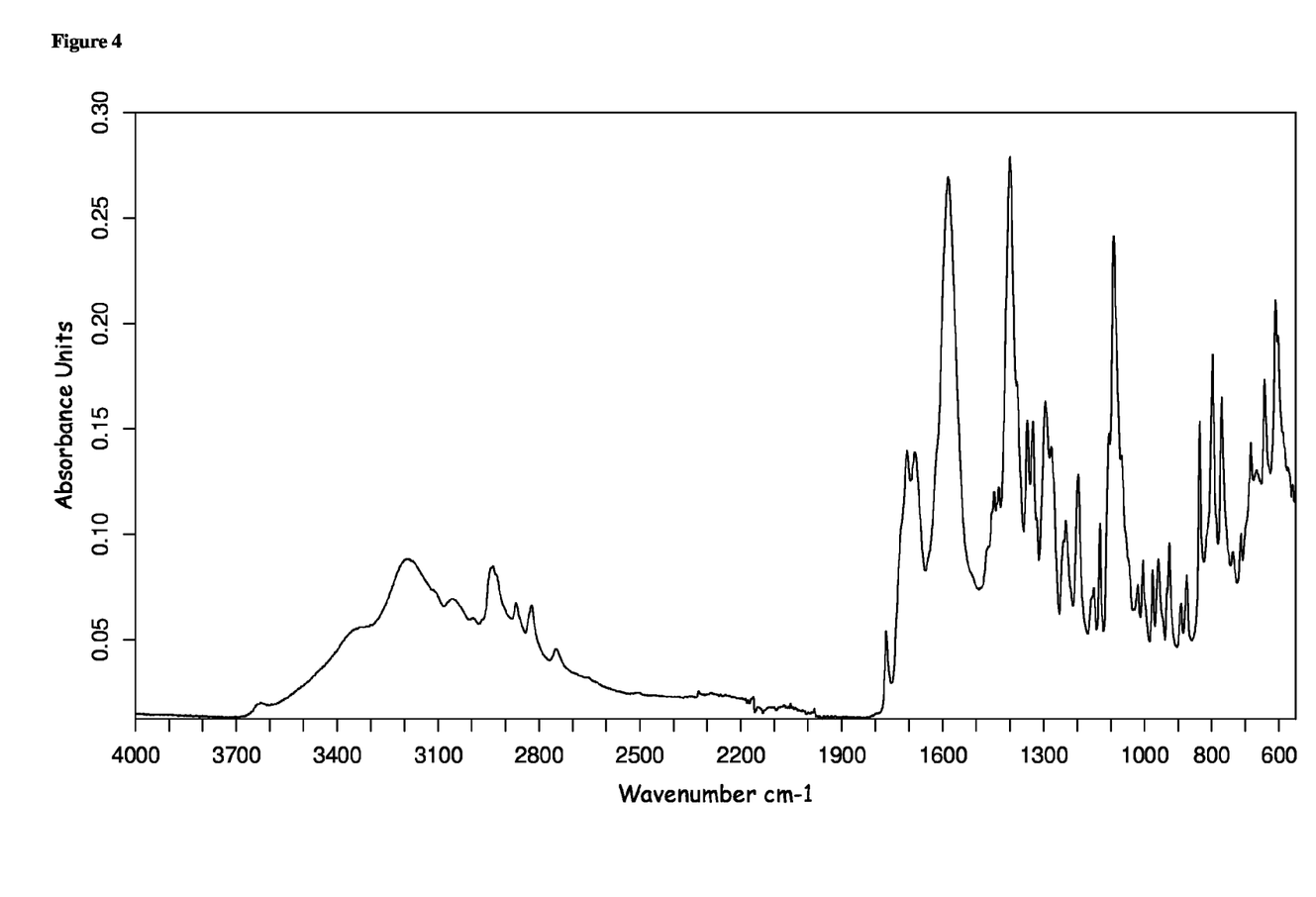

The IR spectrum of the product is shown in FIG. 4.

The following bands are characteristic for the calcium salt (cis-IV, M=Ca, n=2):

1682 cm$^{-1}$, 1583 cm$^{-1}$, 1399 cm$^{-1}$, 1294 cm$^{-1}$, 797 cm$^{-1}$.

Example 10

Using Ba(OH)$_2$

A suspension consisting of 19.84 g (0.1 mol) of the compound (II, A=Me; purity 99.9%; isomer ratio cis/trans=75:25) and 12.358 g (0.038 mol) of Ba(OH)$_2$ octahydrate (97% pure) in 42 ml of water is stirred at 80° C. for 30 minutes. A further 15 ml of water are then added, the mixture is allowed to cool to room temperature and stirred for a further 30 minutes and the solid is filtered off with suction, washed with 10 ml of water and dried. This gives 16.98 g of solid having an isomer ratio cis/trans of 94.2:5.8 and a water content of 10.86% by weight.

Elemental analysis showed a barium content of 14% by weight (theoretical: 25.83%); i.e. the product is predominantly a mixture of (cis-II) and (cis-IV).

Figure 5:
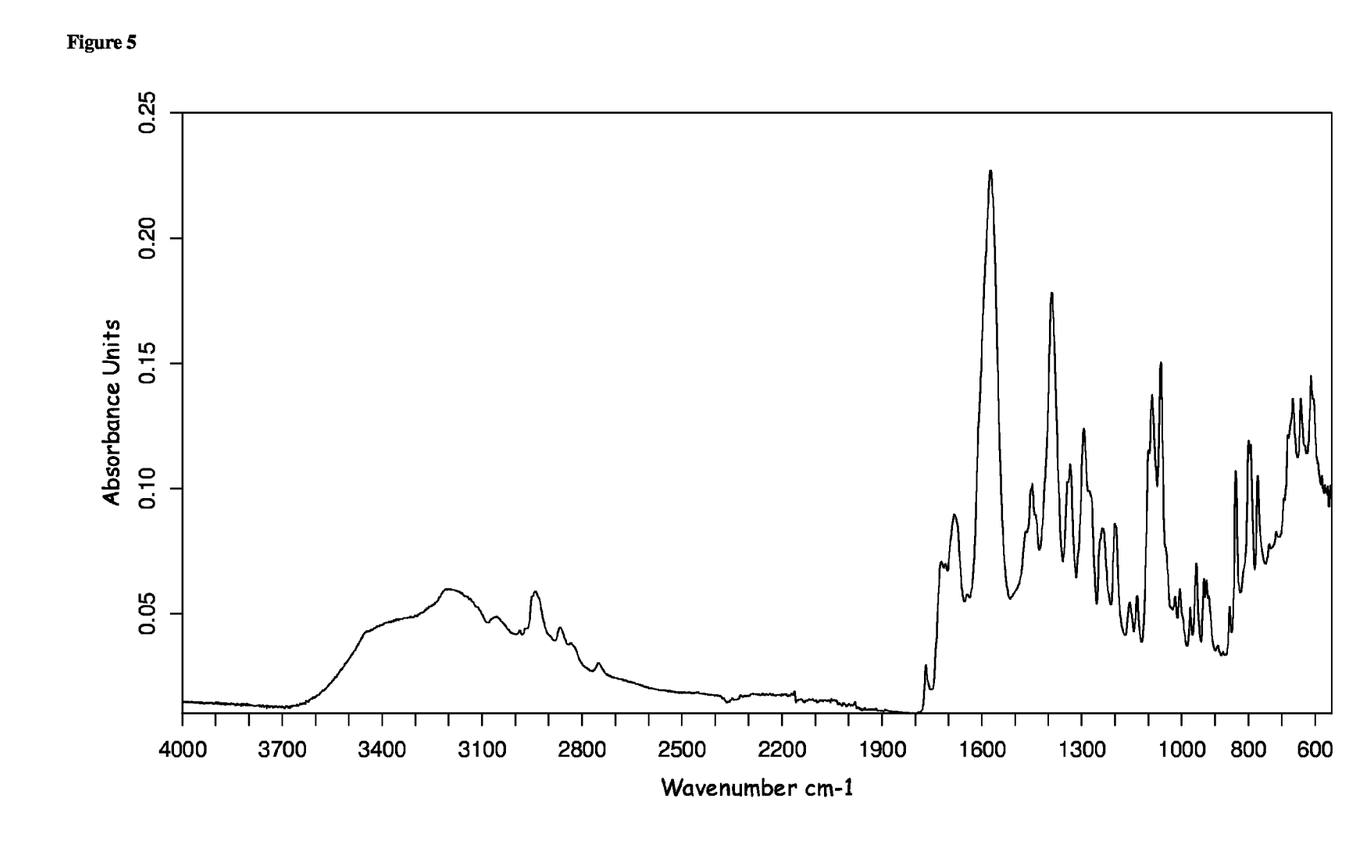

The IR spectrum of the product is shown in FIG. 5.

The following bands are characteristic for the barium salt (cis-IV, M=Ba, n=2):

1682 cm$^{-1}$, 1573 cm$^{-1}$, 1389 cm$^{-1}$, 1293 cm$^{-1}$, 799 cm$^{-1}$.

The invention claimed is:

1. A process for isolating cis-hydantoins of formula (cis-II)

(cis-II)

in which

A represents C$_1$-C$_6$-alkyl, comprising stirring an isomer mixture of formula (II)

(II)

in which A has the meaning mentioned above,
with an aqueous solution of an alkali metal hydroxide or alkaline earth metal hydroxide, and isolating the cis isomer.

2. The process according to claim 1, where A represents C$_1$-C$_4$-alkyl.

3. The process according to claim 1, where A represents methyl, ethyl, propyl, isopropyl, butyl or isobutyl.

4. The process according to claim 1, where A represents methyl.

5. The process according to claim 1, wherein lithium hydroxide, sodium hydroxide, potassium hydroxide, cesium hydroxide, magnesium hydroxide, rubidium hydroxide, calcium hydroxide or barium hydroxide is used.

6. A compound of formula (cis-IV)

(cis-IV)

or a hydrate thereof in which

A represents C$_1$-C$_6$-alkyl,

M represents an alkali metal cation or represents an alkaline earth metal cation and n represents 1 if M is an alkali metal cation or represents 2 if M is an alkaline earth metal cation.

7. A compound of formula (cis-IV) according to claim 6, in which

A represents methyl,

M represents Li$^+$, Na$^+$ or K$^+$ and n represents 1.

8. A compound of formula (cis-IV) according to claim 6, in which

M represents Na$^+$ and n represents 1.

9. A compound of formula (cis-IV) according to claim 6 in the form of a hydrate.

* * * * *